(12) United States Patent
Letourneur et al.

(10) Patent No.: US 8,362,301 B2
(45) Date of Patent: Jan. 29, 2013

(54) METHOD FOR PRODUCING AMINES

(75) Inventors: Didier Letourneur, Rixheim (FR); Stephan Verdier, Lyons (FR)

(73) Assignee: Rhodia Operations, Aubervilliers (FR)

( * ) Notice: Subject to any disclaimer, the term of this patent is extended or adjusted under 35 U.S.C. 154(b) by 71 days.

(21) Appl. No.: 13/062,896

(22) PCT Filed: Sep. 1, 2009

(86) PCT No.: PCT/EP2009/061268
§ 371 (c)(1),
(2), (4) Date: May 31, 2011

(87) PCT Pub. No.: WO2010/028982
PCT Pub. Date: Mar. 18, 2010

(65) Prior Publication Data
US 2011/0230681 A1    Sep. 22, 2011

(30) Foreign Application Priority Data
Sep. 9, 2008 (FR) ...................... 08 04935

(51) Int. Cl.
*C07C 209/48* (2006.01)
(52) U.S. Cl. ....................................... 564/492; 564/491
(58) Field of Classification Search .................. 564/491, 564/492
See application file for complete search history.

(56) References Cited

U.S. PATENT DOCUMENTS
6,677,486 B2 * 1/2004 Ansmann et al. ............. 564/490

* cited by examiner

*Primary Examiner* — Brian J Davis
(74) *Attorney, Agent, or Firm* — SNR Denton US LLP

(57) ABSTRACT

Amine compounds, more particularly diamine compounds, are prepared by hydrogenating compounds including nitrile functions. The preparation can include the use of a hydrogenation catalyst, adapted for the hydrogenation of nitrile compounds into amine compounds, including Raney nickel as well as iron, chromium, and zinc as doping elements.

8 Claims, No Drawings

METHOD FOR PRODUCING AMINES

This application claims priority under 35 U.S.C. §119 of FR 0804935, filed Sep. 9, 2008, and is the United States national phase of PCT/EP2009/061268, filed Sep. 1, 2009, and designating the United States (published in the French language on Mar. 18, 2010, as WO 2010/028982 A1; the title and abstract were also published in English), each hereby expressly incorporated by reference in its entirety and each assigned to the assignee hereof.

The present invention relates to a process for manufacturing amine compounds, more particularly diamine compounds, by hydrogenation of compounds comprising nitrile functional groups.

It relates more particularly to the manufacture of hexamethylenediamine by hydrogenation of tetramethylene dicyanide.

Hexamethylenediamine is a compound used in numerous applications, the main ones of which are the manufacture of polyamides such as polyhexamethylene adipamide, and the manufacture of diisocyanates.

Several processes for manufacturing hexamethylenediamine have been proposed, which generally consist of a hydrogenation of a compound comprising nitrile functional groups such as tetramethylene dicyanide in the presence of a hydrogenation catalyst. Two types of process are utilized industrially that use different catalysts and different temperature and pressure conditions.

Thus, a first type of hydrogenation process that is utilized and described in the literature consists in hydrogenating nitrile compounds in the presence of ammonia and under high pressure, with a ruthenium-based catalyst for example.

A second type of process consists in carrying out the hydrogenation of nitrile compounds under a pressure close to atmospheric pressure and at a not very high temperature, in the presence of a basic compound and a catalyst based on Raney nickel.

In the latter type of process, the hydrogenation of nitrile compounds to amines takes place in the presence of a catalyst based on optionally doped Raney nickel. These catalysts are prepared by the leaching of aluminium, from aluminium-rich Ni—Al alloys, in a strongly alkaline medium. The catalysts obtained are composed of agglomerates of nickel crystallites, having a high specific surface area and a variable residual aluminium content.

Modification of the structural and electronic factors of Raney nickel, by addition of metals to the nickel-aluminium alloy, has already been envisaged. Conventionally, the addition of a dopant is carried out by introducing this dopant into a molten Ni—Al precursor alloy. This is metallurgical doping. Thus, the doping of Raney nickel by various metallic promoters (Fe, Co, Cr, Mn, V, Mo, Zr, Ta, Ti), and also their effects as regards the activity, the selectivity and the stability of the catalyst, are the subject of a rich scientific and technical literature.

The article by Freidlin et al. (*Russian Chemical Review*, vol. 33, No. 6, June 1964) relates to the catalytic reduction of dinitriles and lists a certain number of doped Raney catalysts used under varied hydrogenation conditions (temperature, hydrogen pressure ($P_{H_2}$), reaction medium). Catalysts based on Raney nickel doped with chromium, with copper or with titanium are especially mentioned.

Patent FR-A 2 068 953 relates to Raney Ni catalysts doped with chromium via a metallurgical route.

However, the use of a Raney nickel doped with chromium does not make it possible to achieve negligible contents of impurities in the nitrile hydrogenation medium such as, for example, a low concentration of diaminocyclohexane (DCH). However, these impurities such as DCH are particularly troublesome since they have substantially the same boiling point as the targeted amines and are therefore very difficult to separate.

There is therefore an industrial need for optimization of the conditions for the hydrogenation of nitriles to amines, in particular of dinitriles to amino nitriles and/or diamines, by means of catalysts of the doped Raney Ni type, especially with respect to the operating conditions and also the activity, the selectivity and the stability of the final catalyst.

Such an optimization constitutes one of the essential subjects of the present invention, which comprises a process for the hydrogenation of nitriles to amines that is easy to use, non-polluting, economic and that makes it possible, on the one hand, to achieve amine selectivities of greater than 90% expressed relative to the initial nitrile substrate and, on the other hand, to reduce as much as possible the formation of impurities, especially the formation of DCH.

The subject of the invention is especially a process for manufacturing diamine compounds by hydrogenation of compounds comprising nitrile functional groups, such as dinitrile compounds, by reaction with hydrogen or a gas that contains molecular hydrogen in the presence of a hydrogenation catalyst based on Raney nickel, characterized in that the catalyst comprises Raney nickel and, as metallic dopant elements, iron, chromium and zinc.

According to one preferred feature of the invention, the weight composition of the catalyst, expressed by weight of the metallic element, is the following:

Concentration by weight of iron between 0.3% and 3%.
Concentration by weight of chromium between 0.5% and 5%.
Concentration by weight of zinc between 0.5% and 5%.
Concentration by weight of aluminium between 2% and 10%.
The balance to 100% is nickel.

More advantageously still, the weight concentration of the catalyst according to the invention is the following:

Concentration by weight of iron between 1% and 2%.
Concentration by weight of chromium between 1.5% and 2.5%
Concentration by weight of zinc between 1% and 3%.
Concentration by weight of aluminium between 5% and 7%.
The balance to 100% is nickel.

The doped Raney Ni catalyst used in this process generally originates from a molten Ni—Al precursor alloy (Ni content of 28 to 59% by weight), to which metallic dopant elements are added: iron, chromium and zinc, according to a doping procedure known as a "metallurgical" doping procedure. After cooling, the doped precursor alloy is subjected, in a conventional manner, to an alkaline attack that gives rise to a greater or lesser removal of aluminium and, optionally, of a fraction of the dopant element.

The starting alloys used are, advantageously, chosen from the following forms of binary nickel/aluminium combinations: $NiAl_3$, $Ni_2Al_3$ and proeutectic $Al/NiAl_3$.

The doping of the Raney Ni catalyst may also be carried out via a chemical route. Thus, at least one of the dopants may be added to the composition via this doping method. It is also possible to introduce all of the dopants via this "chemical" doping.

According to a first embodiment of chemical doping, the Raney Ni catalyst is impregnated with a solution containing a precursor of the dopant element. The various standard impregnation methods, known to a person skilled in the art, are possible. The impregnation consists in mixing the catalyst with a solution of the precursor of the dopant. Most of the solvent is evaporated then the catalyst is heat treated and optionally washed with water.

According to a second embodiment of the chemical doping process, the dopant element is precipitated on the Raney Ni catalyst. In this case, the Raney Ni catalyst is suspended in a solvent. A compound, a precursor of the dopant, is added to the suspension then precipitated onto the catalyst. Depending on the nature of the precursor, the precipitation is obtained by, for example, modifying the pH of the suspension by adding a base or by increasing the temperature of the medium over a time that varies from 0.5 to 10 h at a temperature between room temperature (around 20-25° C.) and the boiling point of the solvent used. After settling of the catalyst, the supernatant liquid is extracted and the catalyst is washed with water.

In these two embodiments of chemical doping, the solvent used is, preferably, water. The use of organic solvents is possible depending on the solubility of the precursor compound of the dopant. As precursors of the dopant, it is possible to use organic or inorganic compounds. As examples of organic compounds, mention may be made of metal carboxylates or metal alcoholates. As examples of inorganic compounds, mention may be made of chlorides, nitrates, sulphates, hydroxides or oxides. As a base, it is possible to use various basic compounds such as amines or alkali or alkaline-earth metal carbonates and hydroxides. Preferably, sodium hydroxide or potassium hydroxide is used.

Finally, according to a last embodiment, the precursor compound of the dopant may be introduced during the alkaline attack of the Raney alloy. The Raney alloy is suspended in an aqueous solution of sodium hydroxide in order to obtain a pH of greater than 10, preferably of greater than 12. The precursor compound of the dopant is added to the suspension and the temperature is adjusted between 90 and 100° C. for a period of 0.5 h to 10 h. After settling or sedimentation of the catalyst, the supernatant liquid is extracted and the catalyst is washed with water.

The hydrogenation process of the invention applies, more particularly but not limitingly, to nitrile compounds of formula (I):

NC—R—CN        (I)

in which R represents a linear or branched alkylene or alkenylene group having from 1 to 12 carbon atoms, or a substituted or unsubstituted arylene or aralkylene or aralkenylene group.

Preferably, in the process of the invention dinitrile compounds of formula (I) are used in which R represents a linear or branched alkylene radical having from 2 to 6 carbon atoms.

As examples of such dinitrile compounds, mention may especially be made of adiponitrile or tetramethylene dicyanide, methylglutaronitrile, ethylsuccinonitrile, malononitrile, succinonitrile and glutaronitrile and mixtures thereof, especially the adiponitrile, methylglutaronitrile and ethylsuccinonitrile mixtures that originate from one and the same process for the synthesis of adiponitrile.

Introduction of the nitrile substrate, for example adiponitrile, into the reaction medium is carried out while observing a concentration between 0.001% and 30% by weight relative to the total weight (w/w) of the reaction medium and preferably between 0.1% and 20% w/w.

Preferably, the strong base used is chosen from the following compounds: LiOH, NaOH, KOH, RbOH, CsOH and mixtures thereof.

In practice, use is preferably made of NaOH and KOH, for a good performance/price compromise.

The hydrogenation reaction medium is preferably liquid. It may contain a solvent suitable for dissolving the nitrile substrate to be hydrogenated, knowing that this conversion takes place more readily when said substrate is in solution.

According to one preferred embodiment of the process according to the invention, use is made of an at least partially aqueous, solvent-free, liquid reaction medium. Water is generally present in an amount less than or equal to 50% by weight, advantageously less than or equal to 20% by weight, with respect to the total reaction medium. More preferentially still, the water content of the reaction medium is between 0.1 and 15% by weight with respect to all the constituents of said medium.

To complement or substitute for the water, it is possible if appropriate to provide at least one other solvent, of alcohol and/or amide type. Alcohols which are more particularly suitable are, for example, methanol, ethanol, propanol, isopropanol, butanol, glycols, such as ethylene and/or propylene glycol, polyols and/or mixtures of said compounds.

In the case where the solvent consists of an amide, it can be, for example, dimethylformamide or dimethylacetamide.

When it is used with water, the solvent, which is preferably alcoholic, represents from two to four parts by weight per one part by weight of water and preferably three parts per one part of water.

According to another preferred feature of the invention, the amine whose preparation is targeted by the process is incorporated in the reaction medium. It is, for example, hexamethylenediamine when the nitrile substrate is adiponitrile.

The concentration of the targeted amine in the reaction medium is advantageously between 50% and 99% by weight with respect to the whole of the reaction medium and, more preferentially still, is between 60% and 99% by weight.

The amount of base in the reaction medium varies according to the nature of the reaction medium.

When the reaction medium contains only water and the targeted amine as liquid solvent medium, the amount of base is advantageously greater than or equal to 0.1 mol/kg of catalyst, preferably between 0.1 and 2 mol/kg of catalyst and more preferentially still between 0.5 and 1.5 mol/kg of catalyst.

In the case where the reaction medium comprises water and an alcohol and/or an amide, the amount of base is greater than or equal to 0.05 mol/kg of catalyst, is preferably between 0.1 and 10.0 mol/kg and more preferentially still between 1.0 and 8.0 mol/kg.

Once the composition of the reaction medium and the choice of the catalyst have been decided on, these two components are mixed and this mixture is then heated at a reaction temperature less than or equal to 150° C., preferably less than or equal to 120° C. and, more preferentially still, less than or equal to 100° C.

In concrete terms, this temperature is between room temperature (approximately 20° C.) and 100° C.

Prior to, simultaneously with or subsequent to the heating, the reaction chamber is brought to the appropriate hydrogen pressure, that is to say, in practice, between 0.10 and 10 MPa.

The duration of the reaction is variable according to the reaction conditions and the catalyst.

In a batch operating mode, it can vary from a few minutes to a number of hours.

In a continuous operating mode, which it is entirely possible to envisage for the process according to the invention, the duration is obviously not a parameter which can be set.

It should be noted that a person skilled in the art can adjust the chronology of the stages of the process according to the invention, depending on the operating conditions. The order given above only corresponds to a preferred, but non-limiting, form of the process according to the invention.

The other conditions which govern the hydrogenation (in continuous or batch mode) in accordance with the invention involve technical arrangements which are conventional and known in themselves.

By virtue of all the advantageous arrangements mentioned above, the process of the invention makes it possible to hydrogenate nitrile substrates to amines in a selective, fast, convenient and economical way, with a formation of impurities, especially of DCH, which is much lower than that obtained with a Raney nickel catalyst doped with chromium or with iron and chromium.

This process is perfectly suited for converting adiponitrile to hexamethylenediamine, which is the monomer used in particular in the synthesis of polyamide PA-6,6.

The invention will be better understood and its advantages and its embodiment variants will clearly emerge from the following examples which illustrate, in a non-limiting way, the hydrogenation process according to the invention.

EXAMPLE 1

In this example, the preparation of a Raney Ni catalyst doped with iron and chromium is described. This catalyst will be used as a reference catalyst.

Manufacture of the Alloy:

In a crucible, 75 kg of aluminium ingots are melted at a temperature of around 800° C. 75 kg of nickel and 2.7 kg of an iron/chromium alloy are added to the crucible and the temperature is brought to 1450° C. The medium is homogenized. The molten alloy obtained is cast in ingot moulds, cooled, demoulded, crushed and ground to obtain a powder.

The weight composition of the alloy is the following:
Ni: 47.80%
Al: 50.15%
Fe: 0.85%
Cr: 1.20%

Alkaline Attack:

Introduced into a reactor equipped with a stirrer are 0.5 l of 30 wt % aqueous sodium hydroxide. The temperature of the medium is brought to 97° C. and the top of the reactor is purged with argon. 50 g of alloy powder are gradually introduced into the reactor still under an argon purge. Once the addition of alloy is complete, the alkaline attack is continued for 3 h. After sedimentation of the catalyst, the supernatant liquid is extracted. The catalyst is washed with water until a pH of 7 is obtained, then stored in a 0.05 mmol/l solution of sodium hydroxide.

The weight composition of the catalyst obtained is the following:
Ni: 88.1%
Al: 8.0%
Fe: 1.5%
Cr: 2.4%
That is to say the weight ratios:
Al/Ni: 9.0%
Fe/Ni: 1.7%
Cr/Ni: 2.7%

EXAMPLE 2

In this example, the preparation of a Raney Ni catalyst doped with iron, chromium and zinc is described.

Introduced into a reactor equipped with a stirrer are 415 ml of a 20 wt % solution of sodium hydroxide and 1.0 g of zinc oxide. The temperature of the medium is brought to 90° C. and the top of the reactor is purged with argon. 81 g of the alloy obtained according to Example 1 are introduced into the reactor with a flow rate of 0.7 g/min. Once the addition of alloy is complete, the alkaline attack is continued for 3 h at a temperature of 98° C. After sedimentation of the catalyst, the supernatant liquid is extracted. The catalyst is washed with water until a pH of 7 is obtained, then stored in a 0.05 mol/l solution of sodium hydroxide.

The weight composition of the catalyst obtained is the following:
Ni: 87.80%
Al: 8.00%
Fe: 1.05%
Cr: 2.15%
Zn: 1.00%
That is to say the weight ratios:
Al/Ni: 9.10%
Fe/Ni: 1.20%
Cr/Ni: 2.45%
Zn/Ni: 1.15%

EXAMPLE 3

In this example, the preparation of a Raney Ni catalyst doped with iron, chromium and zinc is described.

Introduced into a reactor equipped with a stirrer are 415 ml of a 20 wt % solution of sodium hydroxide and 1.67 g of anhydrous zinc chloride. The temperature of the medium is brought to 90° C. and the top of the reactor is purged with argon. 80 g of the alloy obtained according to Example 1 are introduced into the reactor with a flow rate of 0.7 g/min. Once the addition of alloy is complete, the alkaline attack is continued for 3 h at a temperature of 98° C. After sedimentation of the catalyst, the supernatant liquid is extracted. The catalyst is washed with water until a pH of 7 is obtained, then stored in a 0.05 mol/l solution of sodium hydroxide.

The weight composition of the catalyst obtained is the following:
Ni: 87.95%
Al: 8.30%
Fe: 1.10%
Cr: 2.10%
Zn: 1.05%
Cl: <10 ppm
That is to say the weight ratios:
Al/Ni: 9.40%
Fe/Ni: 1.25%
Cr/Ni: 2.40%
Zn/Ni: 1.20%

EXAMPLE 4

In this example the catalytic test of hydrogenation of adiponitrile (AdN) to hexamethylenediamine (HMD) by hydrogen in the presence of the Raney Ni catalyst according to Example 1 is described.

The hydrogenation reaction is carried out in a 300 ml stainless steel reactor equipped with:
  a temperature probe;
  a Rushton self-suction turbine;
  a pressure regulator that makes it possible to keep the pressure in the reactor constant;
  a pump that makes it possible to continuously introduce AdN;
  a syringe driver that makes it possible to continuously introduce the aqueous solution of potassium hydroxide (KOH); and a sequential sampling valve which makes it possible to withdraw the reaction medium.

In this reactor, the following are introduced at the start:

114.5 g of HMD and 16.5 g of demineralised water;

3.5 g of the catalyst obtained according to Example 1; and 0.42 g of a 6.8 mol/l potassium hydroxide solution.

The temperature of the reactor is set at 80° C. The turbine is started up at 1300 rpm. The reactor is purged with nitrogen before being put under 25 bar of hydrogen pressure.

At the time t=0, the continuous injection and withdrawal devices are started up:

injection of AdN into the reactor with a flow rate of 0.45 ml/min;

injection of 400 ppm potassium hydroxide solution with a flow rate of 0.05 ml/min; and withdrawal of 0.63 ml via the sampling valve every minute.

The hydrogen is continuously fed into the reactor via the pressure regulator. The hydrogen consumption is followed over time by monitoring the pressure drop in the hydrogen feed reservoir which makes it possible to measure the activity of the catalyst.

The reaction medium withdrawn is collected in a flask under an inert gas thermostated at 60° C. for the 3 h of the test.

The samples withdrawn periodically during the test are analysed by gas chromatography (GC) in order to monitor the formation of the impurities formed during the hydrogenation of AdN to HMD, more particularly the following two impurities:

diaminocyclohexane (DCH); and bishexamethylenetriamine (BHT).

The GC analysis is carried out using a Hewlett Packard HP 6890 chromatograph equipped with a 30 m CAM capillary column from J&W Scientific.

The experimental conditions are the following:

$H_2$ carrier gas;

injector at 250° C.;

flame ionization detector (FID) at 250° C.;

80% split ratio;

temperature programming: hold at 60° C./4 min—ramp at 4° C./min up to 100° C.—hold at 100° C./5 min—ramp at 10° C./min up to 210° C.—hold at 210° C./2 min—ramp at 10° C./min up to 220° C.—hold at 220° C./27 min.

The GC sample is prepared by mixing:

around 2 g, precisely weighed, of reaction medium;

around 30 mg, precisely weighed, of nonylamine (internal standard); and around 0.5 to 1 ml of methanol.

EXAMPLE 5

In this example the catalytic test of hydrogenation of adiponitrile (AdN) to hexamethylenediamine (HMD) by hydrogen in the presence of the Raney Ni catalyst according to Example 2 is described.

The procedure from Example 4 is followed but using the catalyst according to Example 2.

EXAMPLE 6

In this example the catalytic test of hydrogenation of adiponitrile (AdN) to hexamethylenediamine (HMD) by hydrogen in the presence of the Raney Ni catalyst according to Example 3 is described.

The procedure from Example 4 is followed but using the catalyst according to Example 3.

Table 1 below collates the results obtained during the hydrogenation tests from Examples 4, 5 and 6.

| Catalyst | Example 4 Example 1 | Example 5 Example 2 | Example 6 Example 3 |
|---|---|---|---|
| Initial activity of the catalyst ($10^{-5}$ mol $H_2$/g/s) | 110 | 125 | 120 |
| DCH concentration (ppm) | 1700 | 1250 | — |
| BHT concentration (ppm) | 800 | 475 | — |

These tests clearly demonstrate that the catalyst according to the invention has a catalytic activity that is equivalent to or greater than that of the known catalyst and makes it possible to obtain a more selective reaction by substantially reducing the formation of impurities.

The invention claimed is:

1. A process for manufacturing diamine compounds, the process comprising hydrogenating a compound comprising nitrile functional groups by reaction with hydrogen or a gas comprising hydrogen in the presence of a hydrogenation catalyst, wherein the hydrogenation catalyst comprises Raney nickel, iron, chromium and zinc as dopant elements.

2. The process according to claim 1, wherein the weight composition, expressed by weight of metallic element, of the hydrogenation catalyst is:

Al: from 2'Y° to 10%;

Fe: from 0.3% to 3%;

Cr: from 0.5% to 5%;

Zn: from 0.5% to 5%; and

Ni: balance to 100%.

3. The process according to claim 2, wherein the weight composition of the hydrogenation catalyst is:

Al: from 5% to 7%;

Fe: from 1% to 2%;

Cr: from 1.5% to 2.5%;

Zn: from 1% to 3%; and

Ni: balance to 100%.

4. The process according to claim 1, wherein the compound comprising nitrile functional groups is tetramethylene dicyanide.

5. The process according to claim 1, wherein the diamine compound is hexramethylenediamine.

6. The process according to claim 1, wherein the hydrogenation is carried out in the presence of a basic compound.

7. The process according to claim 1, wherein the hydrogenation reaction is carried out under a pressure between 0.1 MPa and 10 MPa.

8. The process according to claim 1, wherein the hydrogenation reaction is carried out at a temperature between 20° C. and 100° C.

* * * * *